(12) United States Patent
Wood

(10) Patent No.: US 10,041,919 B1
(45) Date of Patent: Aug. 7, 2018

(54) HOUSING FOR RADON DETECTORS

(71) Applicant: Robert Arnold Wood, Greenbank (CA)

(72) Inventor: Robert Arnold Wood, Greenbank (CA)

( * ) Notice: Subject to any disclaimer, the term of this patent is extended or adjusted under 35 U.S.C. 154(b) by 0 days.

(21) Appl. No.: 15/624,005

(22) Filed: Jun. 15, 2017

(51) Int. Cl.
*B42F 13/00* (2006.01)
*G01N 33/00* (2006.01)
*G08B 17/10* (2006.01)
*G01T 1/178* (2006.01)

(52) U.S. Cl.
CPC . *G01N 33/0036* (2013.01); *G01N 2033/0093* (2013.01); *G01T 1/178* (2013.01); *G08B 17/10* (2013.01)

(58) Field of Classification Search
CPC ........ G01N 33/0036; G01N 2033/0093; G01T 1/178; G08B 17/10
USPC ....... 248/222.51, 222.52, 343, 553; 250/253, 250/472.1
See application file for complete search history.

(56) References Cited

U.S. PATENT DOCUMENTS

| | | | | |
|---|---|---|---|---|
| 3,676,570 A * | 7/1972 | Gabb | ....................... | H02G 3/18 174/61 |
| 4,286,159 A * | 8/1981 | Kitta | ....................... | G08B 17/00 250/381 |
| 5,034,869 A * | 7/1991 | Choi | ....................... | F21S 8/04 248/343 |
| 8,100,538 B2 * | 1/2012 | Kuroda | ................ | G03B 21/145 353/70 |
| 8,360,833 B2 * | 1/2013 | Grantham | .......... | H05K 7/20745 361/695 |
| 2010/0073172 A1 * | 3/2010 | Lax | ........................ | G08B 7/062 340/578 |
| 2010/0329885 A1 * | 12/2010 | Criner | ................... | F04D 25/088 416/244 R |
| 2011/0031368 A1 * | 2/2011 | Wang | ...................... | F24F 7/007 248/343 |
| 2013/0157502 A1 * | 6/2013 | Sittenauer | .............. | G08B 17/10 439/546 |
| 2015/0176604 A1 * | 6/2015 | Lin | ....................... | F04D 19/002 248/634 |

* cited by examiner

*Primary Examiner* — Gwendolyn W Baxter
(74) *Attorney, Agent, or Firm* — Elias Borges

(57) ABSTRACT

A wall mounted radon detector mount for an interior room of a building is disclosed. The mount includes a flat plate for permanently mounting to a wall or ceiling of the room and a housing mountable to the flat plate. The housing has an interior space containing at least one radon detector. The mount is provided with a mounting lock for mounting the housing to the flat plate and locking the housing to the plate such that the housing cannot be removed from the mounting plate. A key is provided for engaging the lock to permit the housing to be detached from the flat plate leaving the radon detectors mounted within the housing and accessible.

6 Claims, 4 Drawing Sheets

HOUSING FOR RADON DETECTORS

BACKGROUND

The present disclosure relates to housings for holding and mounting radon detectors. Radon is a naturally occurring radioactive noble gas which can accumulate within residential and commercial buildings. Radon can pose a significant health hazard. For example, elevated levels of radon in a home or workplace can expose people to a significantly increased risk of developing lung cancer. It is estimated that radon is the second leading cause of lung cancer after cigarette smoking. The problems associated with elevated radon levels is a sufficient concern that government agencies such as Health Canada have recommended that all dwellings and workplaces be tested for radon. Radon levels are generally measured in a home or other building by placing a radon detector within the building in a location exposed to air. The radon detector itself does not detect radon directly, rather it detects the alpha radiation emitted by radon as it decays. The detector is usually placed within an environment to be tested for a period of time, usually several days, and then taken away to be analyzed after a predetermined period of time.

To ensure an accurate reading, the detector must be exposed to the air in the environment. Generally, the detector must be positioned in a particular orientation relative to the interior of the building to ensure consistent readings. For example, current Health Canada long term testing protocols require the detector to be placed adjacent an interior wall at a height of 0.8 to 2 m from the floor in the "breathing zone", and at least 50 cm from the ceiling and 20 cm from other objects so as to allow normal air flow around the detector. The detector should be placed approximately 40 cm from an interior wall or 50 cm from an exterior wall.

Mounting the radon detector becomes a concern if accuracy is required. It will be appreciated that placing different radon detectors in different positions and in different locations within the same building may result in the measurement of significantly different radon levels among the detectors even if the radon concentration in the air is uniformly distributed throughout the building. Furthermore, positioning the radon detector within the environment can result in false or inaccurate readings if the radon detector is moved, either deliberately or accidentally, during the course of the test period. A means for solving the problems associated with placing radon detectors in buildings is required if accurate radon testing is to be implemented on a large scale.

SUMMARY

An apparatus embodying the aspects of the present invention is described further below. The apparatus is a mount for mounting one or more radon detectors onto a structural flat surface such as a wall or ceiling within the interior of a building. The apparatus consists of a housing having opposite first and second sides and a peripheral edge with at least one detector mount formed on the first side. A flat plate is also included, the flat plate having opposite first and second sides, the fist side of the flat plate configured to mount to the structural flat surface. The flat plate and housing are configured such that they can be mounted to each other and locked together. The flat plate and housing are further configured such that when locked together, they form an interior space between the fist side of the housing and the second side of the flat plate, the interior space being dimensioned to contain the radon detectors. The flat plate and housing are further configured to form an air passage permitting outside air from outside the housing to pass into the interior space. The flat plate and housing are further configured such that when the housing is unlocked and decoupled from the flat plate the radon detector mounted to the housing is exposed.

With the foregoing in view, and other advantages as will become apparent to those skilled in the art to which this invention relates as this specification proceeds, the invention is herein described by reference to the accompanying drawings forming a part hereof, which includes a description of the preferred typical embodiment of the principles of the present invention.

BRIEF DESCRIPTION OF THE DRAWINGS

In the drawings, like characters of reference indicate corresponding parts in the different figures.

DETAILED DESCRIPTION

Figure 1:
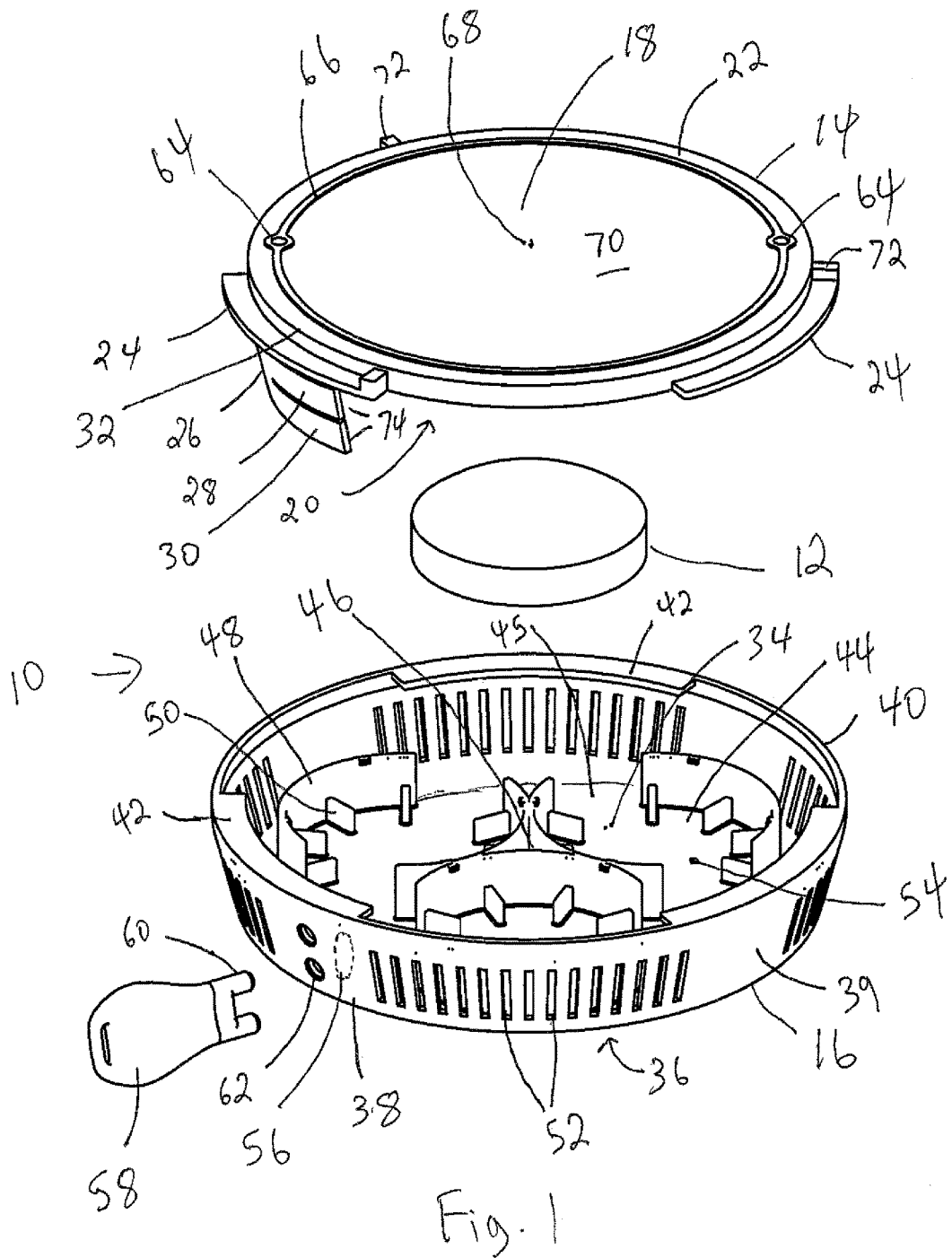
FIG. 1 is an exploded view of the radon detector mount made in accordance with the present invention showing the underside of the flat plate portion and the inside of the housing portion.

Referring firstly to FIG. 1, a mount for mounting one or more radon detectors 12 to a structural flat surface such as a wall or ceiling (not shown) is shown generally as item 10 and consists of a flat wall plate 14 which is configured to be removably coupled to a housing 16. Flat plate 14 has opposite sides 18 and 20 and peripheral edge 22. Tongue in groove connector elements 24 are provided at peripheral edge 22. Ann 26 projects from peripheral edge 22 away from side 20. Elongated parallel fingers 28 and 30 project from aim 26 and extend along portion 32 of peripheral edge 14 parallel to portion 32. Fingers 28 and 30 and arm 26 are preferably positioned adjacent a tongue and groove connector element 24.

Housing 16 consists of a substantially flat portion having opposite sides 34 and 36 and peripheral edge 36 with wall 39 projecting from the peripheral edge and having a lip 40. Tongue in groove connector elements 42 are formed on lip 40 and are configured to be complimentary with tongue in groove connector elements 24.

A plurality of radon detector mounts 44 are formed on side 34, each detector mount configured to releasably retain radon detector 12. In the present embodiment, three radon detector mounts 44 are arranged in a circular configuration around a central portion 46. Each mount 44 consists of a pair of C shaped resilient members 48 configured to snugly receive and hold the radon detector. A gap 45 is left between the edges of C shaped member 48 to permit the radon detectors to be more easily inserted and removed from the radon detector mounts. A plurality of fins 50 are positioned in mount 44 so that an air gap is retained between the radon detector 12 and side 34 of the housing when the radon detector is mounted to the detector mount. This air gap permits air to circulate around the radon detector ensuring a more accurate reading is measured by the detector. Air passageways 52 are formed on wall 39 to permit air to pass through the passageways and into interior space 54 of housing 16.

Figure 2:
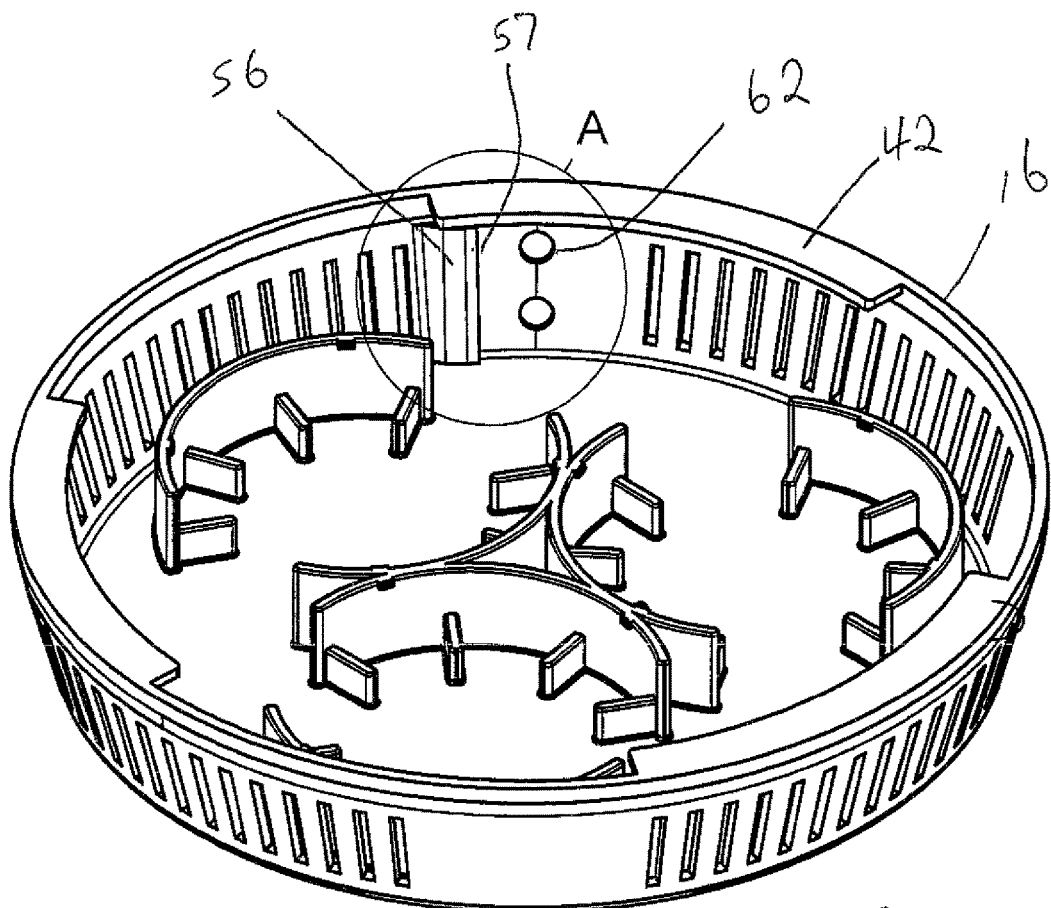
FIG. 2 is an isometric view of the housing portion of the radon detector shown in FIG. 1 showing the interior of the housing portion.
Figure 3:
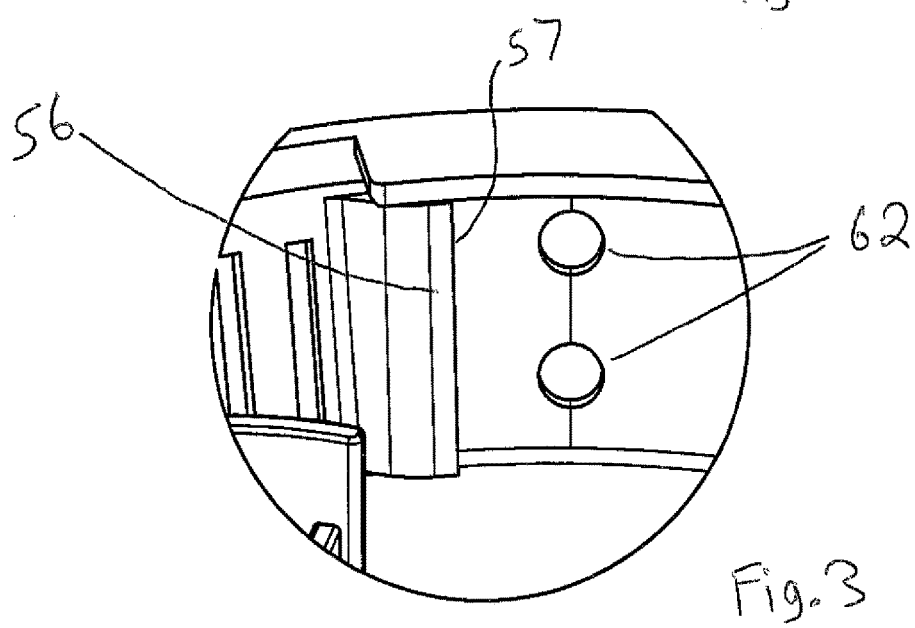
FIG. 3 is a perspective view of part A of FIG. 2.
Figure 4:
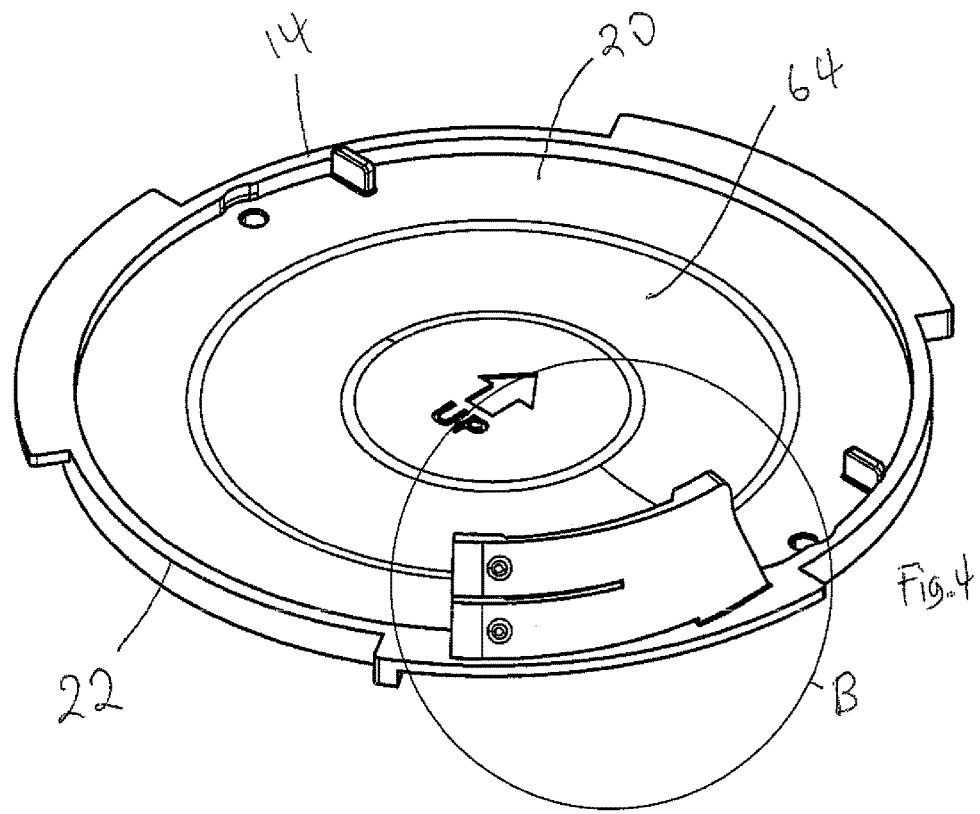
FIG. 4 is a perspective view of the underside of the flat portion of the radon detector mount shown in FIG. 1.
Figure 5:
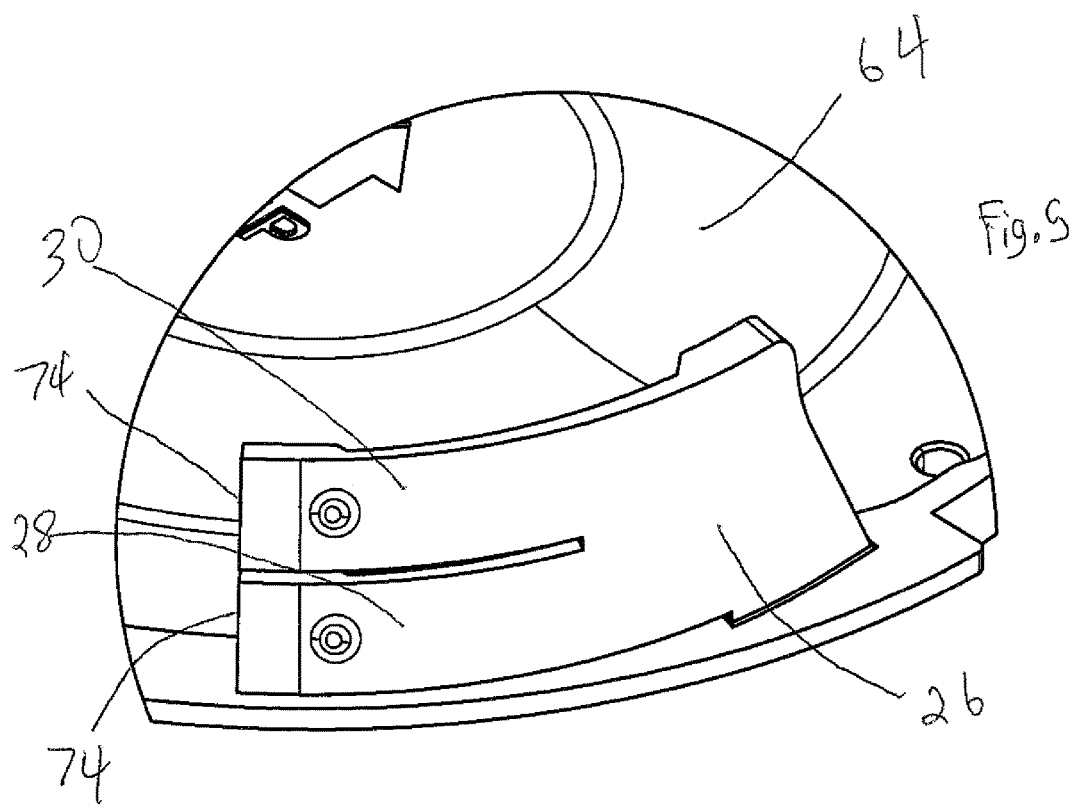
FIG. 5 is a perspective view of part B of FIG. 4.

Flat plate 14 can be mounted to a flat surface in an interior of a building such as a wall or ceiling so that side 18 abuts against the flat surface. Flat plate 14 is provided with screw holes 64 to enable a person to screw the flat plate to the wall thereby permanently affixing the flat plate to the wall. An annular ridge 66 is positioned concentric to centre point 68 and screw holes 64 pass through ridge 66. Ridge 66 is slightly raised relative to flat surface 70 ensuring that any bumps or imperfections on the wall or ceiling the flat plate is mounted to won't cause the flat plate to be mounted at a slight angle relative to the wall or ceiling. This is important in ensuring that the radon detector mount is consistently mounted in the same orientation from building to building. After flat plate 14 is mounted to the wall or ceiling, housing 16 can be mounted thereto by positioning the housing adjacent the flat plate and positioning the housing such that tongue in groove connector elements 42 align with tongue in groove connector elements 24. The housing can then be rotated in a first direction causing the tongue in groove connectors to engage until their movement is arrested by stops 72. A ratchet locking mechanism is included in the design of housing 16 and flat plate 14 to prevent rotation of the housing in a direction opposite the first direction thereby preventing the housing from accidentally being removed from the flat plate. The ratchet lock mechanism consists of flexible fingers 28 and 30 and projecting tooth 56. Projecting tooth 56 is an angular protrusion extending from wall 39 and projecting into interior 54. FIGS. 2 and 3 show a clearer view of projecting tooth 56 while FIGS. 4 and 5 show a clearer view of fingers 28 and 30. Referring back to FIG. 1, fingers 28 and 30 are shaped and configured to be positioned very close to the inside surface of wall 39 and are made sufficiently flexible so that when the housing is rotated into its locked mounting position, the flexible fingers are deflected by tooth 56 until tips 74 of the flexible fingers pass tooth 56, at which point the fingers resiliently rebound back to their original shape. Projecting tooth 56 presents a square angle (item 57 on FIGS. 2 and 3) to the tips 74 of fingers 28 and 30 so that if the housing is rotated opposite the first direction, tips 74 engage tooth 56 thereby preventing housing 16 from being rotated further and decoupled from flat plate 14. Fingers 28 and 30 act like a pawl of a ratchet mechanism permitting rotation of housing 16 in only one direction relative to flat plate 14. A pair of apertures 62 are positioned adjacent tooth 56 so that when housing 16 is fully coupled and locked to flat plate 14, fingers 28 and 30 are positioned immediately adjacent apertures 62. Key 58 can be used to unlock the ratchet mechanism. Key 58 has prongs 60 which are dimensioned to pass through apertures 62 and simultaneously engage fingers 28 and 30 permitting the fingers to be deflected sufficiently that tips 74 clear tooth 56 permitting housing 16 to be rotated out of its locked position. A ratchet lock having two independent pawls is more secure because both pawls have to be disengaged before the lock can be released. If the lock consisted of a single pawl, it could more easily be defeated.

Referring now to FIG. 4, side 20 of flat plate 14 has an annular groove 64 concentric with peripheral edge 22. Groove 64 permits radon detector 12 to be positioned close to side 20 without touching the side so as to leave an air gap between the radon detector and the flat plate. This ensures that radon detector 12 is surrounded with air permitting a more accurate sampling of the air for the presence of radon.

Referring back to FIG. 1, the present design makes it easy to mount a plurality of radon detectors to a wall, ceiling or other structural flat surface in the interior of a building. To use the mount, flat plate 14 is first mounted to the surface of a wall or ceiling. Preferably, the flat plate is mounted to a wall in the breathing zone of a room, which will generally be a few feet below the ceiling but several feet above the floor (see FIG. 3). The flat plate is attached by means of screws or nails through apertures 64. After flat plate 14 is mounted, one or more fresh radon detectors 12 are inserted into the interior of housing 16. Since housing 16 is not yet attached to the flat plate, inserting the radon detectors is very easy. Radon detectors 12 are inserted between C shaped members 48 which are dimensioned to snugly retain the radon detector and hold it firmly. In the present embodiment, up to three separate radon detectors can be mounted to housing 16. When the radon detectors are mounted to housing 16, the housing can be mounted to plate 14 by aligning tongue in groove connector elements 24 and 42 and moving the housing relative to the flat plate in the correct direction. When fully positioned, the ratchet lock formed by fingers 28 and 30 and tooth 56 lock the housing in place. The device is then left alone for a period of time ranging from a few days to several weeks as mandated by the appropriate radon testing protocols. After the time period has expired, the radon detectors can then be collected and sent for testing to determine the radon levels of the air inside the room where the radon detectors were mounted. To collect the radon detectors, key 58 is used to deflect fingers 28 and 30 while housing 16 is turned. Key 58 makes it very easy to deflect both fingers 28 and 30 simultaneously while also rotating the housing. When rotated sufficiently such that tongue in groove connector elements 42 and 24 are no longer engaged, the housing can be released from flat plate 14 with the radon detectors remaining in the housing and exposed for access. The radon detectors can then be easily removed from the housing and collected.

Figure 6:
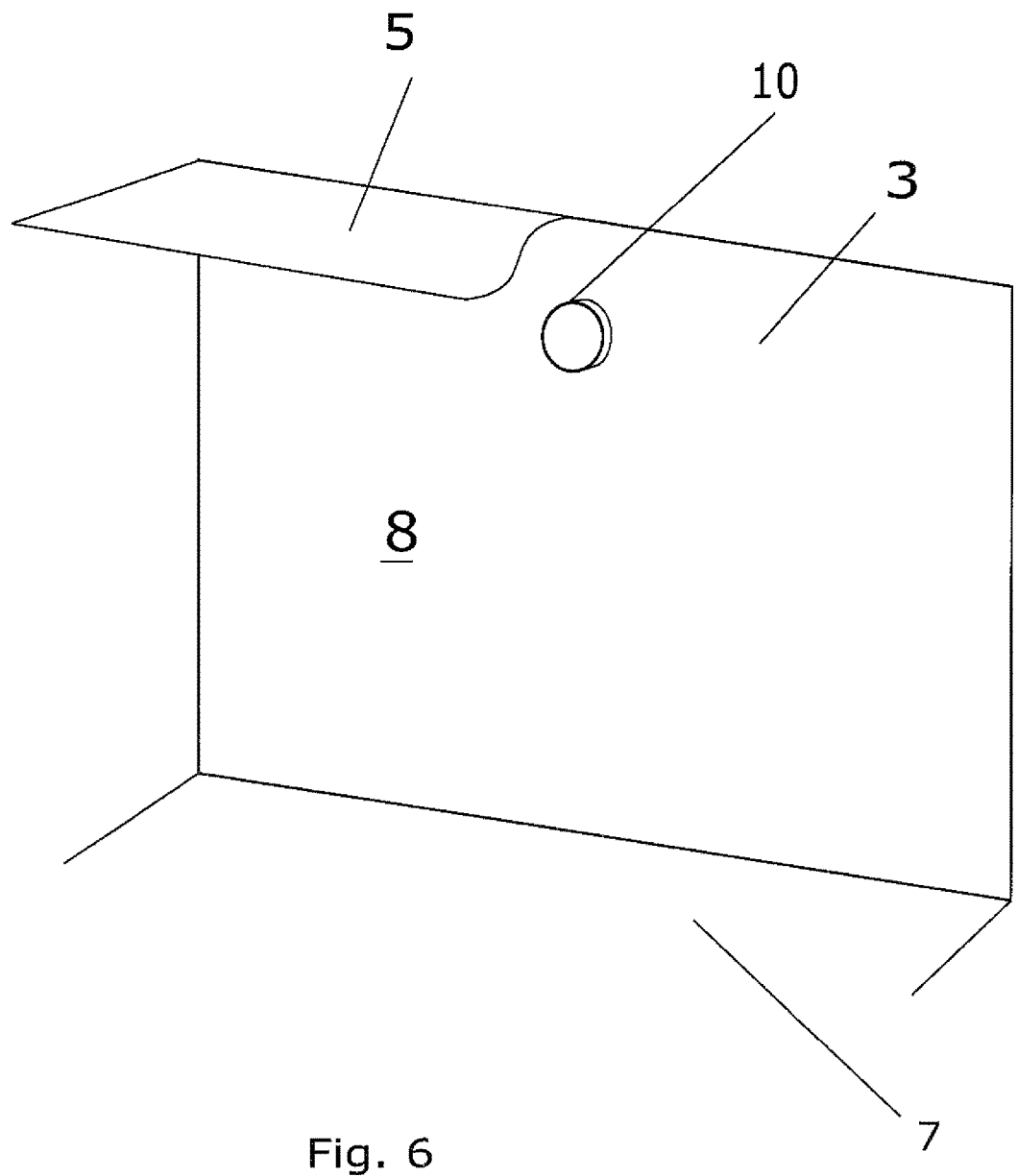
FIG. 6 is a side view of radon detector mount shown in FIG. 1 mounted to a wall in the interior of a room.

Referring now to FIG. 6, the installation of the radon detector mount in a room shall now be discussed. Radon detector mount 10 can be mounted to flat surface 8 of wall 3 at a predetermined position between floor 7 and ceiling 5. To ensure that the radon detectors contained in radon detector mount 10 are exposed to the air in the area where air is most likely to be breathed by people in the room (the breathing zone), mount 10 is mounted at least 50 cm from ceiling 5 and at least 2 m from floor 7. To ensure consistent and accurate radon measurements, mount 10 is placed at an exact distance from the floor, say 2 m, in every room and the radon exposure in each radon detector measured against a plurality of reference detectors (not shown) which were calibrated at the same distance from the floor. This will take into consideration that each room may have different ceiling heights. To mount radon detector mount 10 to wall 3, the flat plate portion (item 14 in FIG. 1) is first mounted to the wall by means of nails, screws or other fastening means known generally in the art. The housing portion (item 16 in FIG. 1) is then loaded with the radon detectors and attached to the flat plate and locked into place. After a suitable interval of time ranging from several days to a few months, the radon detectors can be easily removed to be analysed.

The present device has several unique advantages. Firstly, the design makes it very simple and easy to mount a plurality of radon detectors in a specific and controllable orientation in a room. The design permits air to circulate around the entire radon detector making for more accurate measurement of the radon levels in the air by the radon detector. Since the radon detectors are positioned at an exact distance from the wall or surface by virtue of the shape of flat plate 14 and housing 16, consistent measuring conditions can be easily reproduced regardless of which room in which building is being tested for radon. Since the radon detector mount positions the radon detectors in the same orientation relative to the wall or ceiling, a more accurate and consistent measuring of the radon levels in the interior air of the room where the mount is contained can be measured.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art.

What is claimed is:

1. A mount for mounting at least one radon detector to an interior wall and ceiling of a building comprising:
   a. a cylindrical housing having a circular flat bottom with opposite first and second sides, the flat bottom having a peripheral edge, the housing having a wall extending away from the flat bottom along the peripheral edge and circumscribing the first side of the flat bottom to form a large opening with a peripheral lip, at least one air passage formed on the wall, a protrusion formed on an inside surface of the wall;
   b. at least one detector mount for securely holding the radon detector formed on the first side of the flat bottom;
   c. a flat plate having opposite first and second sides and a circular peripheral edge, the first side of the flat plate configured to be mounted to the wall and ceiling, an arm formed on a portion of the circular peripheral edge, the arm projecting away from the second side of the flat plate, the arm having a pair of fingers extending from the arm and extending parallel to and adjacent with a section of the circular peripheral edge, the fingers being resiliently flexible;
   d. the peripheral edge of the flat plate and the peripheral lip of the wall having complementary curved tongue and groove connector elements configured to permit the housing to be mounted to the flat plate by aligning the tongue and groove connectors and rotating the housing relative to the flat plate in a first direction, the protrusion positioned on the inside surface such that the protrusion and the parallel fingers form a pair of parallel ratchet locks preventing the housing from rotating opposite the first direction once the housing has been locked to the flat plate;
   e. a two pronged key configured to operatively couple with the flat plate and the housing to unlock the flat plate from the housing by simultaneously deflecting each of the fingers to permit rotation of the housing opposite the first direction;
   f. the flat plate and the housing configured to form an internal space defined by the first side of the flat plate, the first side of the housing and the wall of the housing when the flat plate and housing are locked together, the first side of the flat plate having an annular groove, the annular groove, housing and flat plate all configured to accommodate the radon detectors mounted to the first side of the housing;
   g. the flat plate configured to be rigidly mounted to the wall and ceiling.

2. A mount for mounting at least one radon detector within an inside space of a building by mounting said at least one radon detector to an interior wall and ceiling of said building, the mount comprising:
   a. a housing having first and second sides and a peripheral edge;
   b. at least one detector mount for securely and releasably holding the radon detector, the detector mount formed on the first side of the housing;
   c. a flat plate having opposite first and second sides, the first side of the flat plate configured to be mountable to the wall and ceiling;
   d. the flat plate and housing being configured such that the housing and flat plate can be mounted together to form an enclosed interior space between the first side of the housing and the second side of the flat plate, the interior space dimensioned to contain said at least one radon detector when the flat plate and housing are mounted together, the flat plate and housing being further configured such that when the flat plate and housing are separated from each other said at least one radon detector mounted on the housing is exposed;
   e. the flat plate and housing configured to form at least one air passage coupling the interior space to the inside space of the building, and
   f. a lock formed on the flat plate and housing for preventing the housing from being separated from the flat plate after the housing is mounted to the flat plate, the lock operatively coupled to a key configured to open the lock and permit the housing to be separated from the flat plate when the key engages the lock.

3. The mount defined in claim 2 wherein the flat plate and housing are each provided with complimentary tongue and groove connector elements to permit the housing to be mounted to the flat plate by aligning the tong and groove connector element of the housing with the complimentary tongue and groove connector of the flat plate and moving the housing in a first direction relative to the flat plate, the housing being detachable from the flat plate by moving the housing in a second direction opposite the first direction, the lock comprising a pawl and tooth ratchet configured to allow the housing to travel in the first direction but not the second direction.

4. The mount defined in claim 3 wherein the pawl comprises a pair of flexible parallel fingers formed on the flat plate which are configured to engage a projecting tooth formed on the housing, the housing being configured to enclose the fingers and projecting tooth, the key comprising a member having a pair of parallel prongs projecting from one end of the key, the housing having a pair of adjacent openings positioned adjacent the fingers when the housing is mounted to the flat plate and locked in place, the pair of parallel prongs configured to pass through the pair of adjacent openings to permit the fingers to be deflected sufficiently to release the projecting tooth.

5. The mount defined in claim 4 wherein the first side of the housing has at least three radon detector mounts equally spaced in a circular arrangement around a central point, the second side of the flat plate having an annular groove configured to be co-axially aligned with the central point, the annular groove having a groove width at least as wide as a width of each of the radon detectors.

6. The mount defined in claim 5 wherein each detector mount comprises a pair of C shaped members dimensioned and configured to snugly and firmly hold the radon detector between the C shaped members, the C shaped members being separated by a gap sufficient to permit a user to physically engage the radon detector mounted between the C shaped members, the radon detector mounts having at least one projecting fin for maintaining an air gap between the radon detector and the first side of the housing.

\* \* \* \* \*